United States Patent [19]

Wolfangel

[11] Patent Number: 5,219,556
[45] Date of Patent: Jun. 15, 1993

[54] STABILIZED THERAPEUTIC RADIOPHARMACEUTICAL COMPLEXES

[75] Inventor: Robert G. Wolfangel, Ballwin, Mo.

[73] Assignee: Mallinckrodt Medical, Inc., St. Louis, Mo.

[21] Appl. No.: 549,981

[22] Filed: Jul. 9, 1990

[51] Int. Cl.$^5$ .............................................. A61K 43/00
[52] U.S. Cl. ..................................... 424/1.1; 252/644
[58] Field of Search ................. 424/1.1; 252/632, 645, 252/644

[56] References Cited

U.S. PATENT DOCUMENTS

| | | | |
|---|---|---|---|
| Re. 32,417 | 5/1987 | Burchiel et al. | 424/1.1 |
| 4,062,933 | 12/1977 | Wolfangel | 424/1.1 |
| 4,341,755 | 7/1982 | Lindall | 424/1.1 |
| 4,485,086 | 11/1984 | Wong | 424/1.1 |
| 4,489,053 | 12/1984 | Azuma et al. | 424/1.1 |
| 4,515,766 | 5/1985 | Castronovo et al. | 424/1.1 |
| 4,636,380 | 1/1987 | Wong | 424/1.1 |
| 4,652,440 | 3/1987 | Paik et al. | 424/1.1 |
| 4,778,672 | 10/1988 | Deutsch et al. | 424/1.1 |
| 4,897,255 | 1/1990 | Fritzberg et al. | 424/1.1 |
| 4,898,724 | 2/1990 | Simon et al. | 424/1.1 |
| 4,935,222 | 6/1990 | Deutsch et al. | 424/1.1 |
| 5,001,072 | 3/1991 | Olson | 530/389 X |

FOREIGN PATENT DOCUMENTS 203696 12/1986 European Pat. Off. .
250966 1/1988 European Pat. Off. .

OTHER PUBLICATIONS

Abstract "Radiohalogenation of Antibodies—A Review of Labeling Methods and Their Chemical Consequences, " Reynolds, J. C. at Radiolabeled Monoclonal Antibodies for Imaging and Therapy, Jul. 20-Aug. 1, 1986, Italy.
S. J. Mather and B. G. Ward, *J. Nuclear Medicine* 28: 1034-1036 (1987).
C. F. Meares et al., *Analytical Biochemistry* 142: 68-78 (1984).
B. W. Wistow et al., *J. Nuclear Medicine* 18: 455-461 (1977).

*Primary Examiner*—Robert L. Stoll
*Assistant Examiner*—John M. Covert
*Attorney, Agent, or Firm*—Rothwell, Figg, Ernst & Kurz

[57] ABSTRACT

A method of preparing a stable, therapeutic radiopharmaceutical composition comprised of an alpha- or beta-emitting radionuclide and a ligand by lyophilizing a solution of the complex. The radionuclide preferably has a half-life of at least twelve hours. The invention also is directed to stable lyophilized radiopharmaceutical compositions prepared by this method. The invention is particularly suited to the preparation of radionuclide-labeled antibodies in a stable form which merely requires reconstitution at the point of use.

38 Claims, No Drawings

STABILIZED THERAPEUTIC RADIOPHARMACEUTICAL COMPLEXES

FIELD OF THE INVENTION

The present invention relates to the preparation and stabilization of therapeutic radiopharmaceuticals useful, for example, in cancer treatment. In particular, the present invention relates to the preparation of radioactive therapeutic radiopharmaceuticals in a stable, shippable, lyophilized form. The lyophilized preparations are reconstituted and administered to a patient in need of radiopharmaceutical therapy.

BACKGROUND OF THE INVENTION

Radioactive pharmaceuticals are in common use in imaging studies to aid in the diagnosis of a wide variety of illnesses including cardiac, renal and neoplastic diseases. These pharmaceuticals, known in the art as "imaging agents," typically are based on a gamma-emitting radionuclide attached to a carrier molecule or "ligand." Gamma-emitting radionuclides are the radionuclides of choice for conducting diagnostic imaging studies because, while gamma radiation is detectable with appropriate imaging equipment, it is substantially less-ionizing than beta or alpha radiation. Thus, gamma radiation causes minimal damage to targeted or surrounding tissues.

Radioactive pharmaceuticals now are finding increased use as therapeutic agents for treating neoplastic disorders, especially tumors. Therapeutic radiopharmaceuticals generally incorporate a strong beta- or alpha-emitting radionuclide, the radiation emission being useful in the treatment of certain neoplastic disorders. Such beta or alpha radiation produces intensive ionization paths within a short distance of the radioactive isotope in comparison to the gamma radiation emitted by diagnostic radionuclides, and thus is substantially more damaging to targeted cells.

While the efficacy of radioactive therapeutic agents is established, it is also well known that the emitted alpha or beta particles can cause substantial chemical damage or destabilization to various components in radiopharmaceutical preparations. Emitted alpha and beta particles can produce radiolysis, usually caused by the generation of free radicals, can precipitate proteins present in the preparations, and can cause chemical damage to other substances present in the preparations. The degradation and destabilization of proteins and other components caused by the alpha and beta emitters is especially problematic in aqueous preparations. The degradation or destabilization lowers or destroys the effectiveness of radiopharmaceutical preparations, and has posed a serious problem in the art. Gamma emissions from imaging radionuclides, by contrast, tend to be less damaging and thus are less likely to destabilize the radiopharmaceutical preparations in which they are incorporated.

For diagnostic imaging purposes, radiopharmaceuticals based on a coordination complex comprised of a gamma-emitting radionuclide and a chelate have been used to provide both negative and positive images of body organs, skeletal images and the like. The Tc-99m skeletal imaging agents are well-known examples of such complexes. One drawback to the use of these radioactive complexes is that while they are administered to the patient in the form of a solution, neither the complexes per se nor the solutions prepared from them are overly stable. Consequently, the coordination complex and solution to be administered commonly are prepared "on site," that is, they are prepared by a nuclear pharmacist or health care technician just prior to conducting the study. The preparation of appropriate radiopharmaceutical compositions is complicated by the fact that several steps may be involved, during each of which the health care worker must be shielded from the radionuclide.

The preparation of stable radiopharmaceutical therapeutic agents, due to the type of radioactivity, presents even greater problems. These agents typically are based on a relatively energetic alpha- or beta-emitting radionuclide complexed with a chelate. Frequently, the radionuclide/chelate complex is in turn bound to a carrier molecule which bears a site-specific receptor. Thus, it is known that an alpha- or beta-emitting radionuclide attached to a tumor-specific antibody or antibody fragment can destroy targeted neoplastic or otherwise diseased cells via exposure to the emitted ionizing radiation. Bi-functional chelates useful for attaching a therapeutic radionuclide to a carrier molecule such as an antibody are known in the art. See e.g. Meares et al., Anal. Biochem. 142:68-78 (1984).

For most imaging and therapeutic applications of radiopharmaceutical complexes of the types mentioned above, the nonradioactive portion(s) of the complex is prepared and stored until time for administration to the patient, at which time the radioactive portion of the complex is added to form the radiopharmaceutical of interest. For example, attempts to prepare radionuclide-antibody complexes have resulted in complexes which must be administered to the patient just after preparation because, as a result of radiolysis, immunoreactivity may decrease considerably after addition of the radionuclide to the antibody. In Mather et al., *J. Nucl. Med.*, 28:1034–1036 (1987), a technique for labeling monoclonal antibodies with large activities of radioiodine using the reagent N-bromosuccinimide is described. The authors suggest that the antibodies labeled in this manner be administered to the patient immediately after preparation to avoid losses of immunoreactivity. Other examples of the preparation of the nonradioactive portion of the complex followed by on-site addition of the radioactive portion are disclosed in U.S. Pat. No. 3,984,227 (1976) and U.S. Pat. No. 4,652,440 (1987). Further, in many situations, the radioactive component of the complex must be generated and/or purified at the time the radiopharmaceutical is prepared for administration to the patient. U.S. Pat. No. 4,778,672 (1988) describes, for example, a method for purifying pertechnetate and perrhenate for use in a radiopharmaceutical.

EP 250,966 (1988) describes a method for obtaining a sterile, purified, complexed radioactive perrhenate from a mixture which includes, in addition to the ligand-complexed radioactive perrhenate, uncomplexed ligand, uncomplexed perrhenate, rhenium dioxide and various other compounds. Specifically, the application teaches a method for purifying a complex of rhenium-186 and 1-hydroxyethylidene diphosphonate (HEDP) chelate from a crude solution. Because of the instability of the complex, purification of the rhenium-HEDP complex by a low pressure or gravity flow chromatographic procedure is required. The purification procedure involves the aseptic collection of several fractions, followed by a determination of which fractions should be combined. After combining the appropriate fractions, the fractions are sterile-filtered and diluted prior to injection into the patient. The purified rhenium-HEDP complex should be injected into the patient within one hour of preparation to avoid the possibility of degradation. The rhenium complex may have to be purified twice before use, causing inconvenience and greater possibilities for radiation exposure to the health-care technician.

While the lyophilization process has been applied to various types of pharmaceutical preparations in the past, the notion of lyophilizing alpha- and beta-emitting radiopharmaceutical preparations has not been addressed. In part, this is believed to be due to skepticism of those skilled in the art that such a procedure could be safely carried out. U.S. Pat. No. 4,489,053 (Azuma et al.; Dec. 18, 1984) relates to Tc-99m-based diagnostic imaging agents. The patentee notes that the radioactive agents may be prepared in lyophilized form. Alpha- or beta-emitting radionuclides are not addressed, however.

Thus, there is a need in the art for a method of centrally preparing and purifying a stabilized therapeutic radiopharmaceutical for shipment to the site of use in a form ready for simple reconstitution prior to its administration in therapeutic applications. There is a particular need in the art for a method of centrally preparing and purifying radionuclide-labelled antibodies and antibody fragments, owing to their relatively instable immunoreactivities once in aqueous solution.

SUMMARY OF THE INVENTION

The present invention is directed to a method of preparing a stable radioactive therapeutic radiopharmaceutical composition which comprises forming a complex between an alpha- or beta-emitting radionuclide and a ligand in an aqueous solution and then lyophilizing the solution. The lyophilized radiopharmaceutical composition is reconstituted "on site" by the addition of a suitable diluent to bring the radiopharmaceutical complex into solution at the time of administration to the patient. The present invention further is directed to stable radioactive therapeutic radiopharmaceutical compositions prepared by this method.

DETAILED DESCRIPTION OF THE INVENTION

According to the process of this invention, radionuclides are combined with ligands useful for diagnostic or therapeutic treatment to form radiopharmaceutical complexes in solution or suspension. These complexes then are lyophilized and can be stored until needed for use. This invention allows for the central preparation, purification and shipment of a stabilized form of a radiopharmaceutical complex which merely is reconstituted prior to use. Thus, complicated or tedious formulation procedures, as well as unnecessary risk of exposure to radiation, at the site of use are avoided.

For the purposes of this application, the term "ligand" is taken to mean a bio-compatible vehicle, typically a molecule, capable of binding a radionuclide and rendering the radionuclide appropriate for administration to a patient. Thus, by way of illustration and not limitation, the term ligand encompasses both chelating agents capable of sequestering the radionuclide (usually a chemically-reduced form of the radionuclide) as well as carrier molecules, such as antibodies, antibody fragments or other proteins. The carrier molecules often are specifically targeted at a tumor cell or tumor-specific antigen, an organ or a system of interest or in need of therapy. Carrier molecules may be directly labeled with the radionuclide, or the radionuclide may be bound thereto via a chelate or other binding functionality. The term "complex" is taken to mean, broadly, the union of the radionuclide and the ligand to which it is attached. The chemical and physical nature of this union varies with the nature of the ligand. The term "radiopharmaceutical composition" refers to a composition including the radionuclide-ligand complex as well as suitable stabilizers, preservatives and/or excipients appropriate for use in the preparation of an administrable pharmaceutical.

After a radionuclide-ligand complex is prepared by known methods appropriate to the type of radionuclide and ligand used, aliquots of the radioactive complex are aseptically dispensed into sterile vials and the radioactive product is lyophilized. The resultant pellet contains the radioactive complex in a stable, anhydrous form. The virtually complete absence of water results in a substantial improvement in the stability of the preparation, from both radiochemical purity and chemical purity standpoints, versus prior preparations. The stabilized complex can be prepared several days or weeks in advance, shipped and stored until needed for use.

At the point of use, the radiopharmaceutical compositions of the present invention are prepared for administration to a patient. Such preparation advantageously merely involves reconstitution with an appropriate diluent to bring the complex into solution. This diluent may be sterile water for injection (SWFI), dextrose and sodium chloride injection or sodium chloride (physiological saline) injection, for example. The preferred diluent is water for injection or physiological saline (9 mg/ml) which conforms to the requirements listed in USP XXI.

The radionuclides that can be used in the present invention generally will be alpha or beta emitters of therapeutic value and with a half-life sufficiently long to make the preparation, lyophilization and shipment of the compounds practical. Thus, radionuclides with a half-life of at least 12 hours are preferred. By contrast, the use of Tc-99m, with a half-life of only six hours, or other similarly-lived radioisotopes, becomes impractical. Suitable radionuclides include rhenium-186, rhenium-188, antimony-127, lanthanum-140, samarium-153, iodine-131, strontium-89, radon-222, radium-224, actinium-225, californium-246 and bismuth-210. Rhenium-186 and rhenium-188 are particularly preferred. These rhenium isotopes are known for their chemical versatility and therapeutic value.

The isotopes which are most useable with this process are determined by practical considerations. Again, Tc-99m would be a poor candidate for use since its six-hour half-life makes lyophilization impractical, as the lyophilization step itself generally takes about 24 hours to perform. Another consideration is the ease of preparation of the radiopharmaceutical at the time of use. Those products to which the improvements of this invention are most appropriately applied are those in which the chemistry of the nuclide and ligand are such that preparation of the desired complex is not straightforward or where the resultant complex requires either tedious purification or is stable for a very limited time period after preparation. Where the chemistry of Tc-99m and other gamma-emitting imaging radionuclides renders them very compatible with known "cold kit" technology, the chemistries of the alpha and beta emitters discussed herein are not so forgiving and further complicate the preparation of administrable radiopharmaceutical compositions. Thus, chemical properties and emissions are other considerations for determining the usefulness and practicality of this process in the preparation of a radiopharmaceutical.

Methods for preparing suitable radionuclides are known in the art. Re-186, for example, is formed by irradiating rhenium (Re-185) with neutrons in a nuclear reactor. The Re-186 metal can be oxidized by a strong oxidant, such as a hydrogen peroxide, nitric acid, and the like to form a solution of perrhenate ($ReO_4^-$). This solution then can be neutralized with a strong base, such as ammonia, potassium hydroxide or sodium hydroxide, as required. The formed solution includes perrhenate-186 together with the by-products of the oxidation of the rhenium metal along with the salts generated by the neutralization.

An aqueous crude solution of perrhenate-188 can be formed in this same manner with the exception that the rhenium starting material would be Re-187 rather than Re-185. A more preferred method for obtaining Re-188 is by eluting a tungsten-188/Re-188 generator with a saline solution or the like.

The perrhenate generated as described above may be further purified. One method of purification is described in U.S. Pat. No. 4,778,672, incorporated herein in its entirety, which discloses the use of a lipophilic counter cation to separate the perrhenate from an aqueous mixture of crude perrhenate by preferential sorption in a liquid/liquid or liquid/solid separation.

The unpurified or purified perrhenate (or other selected radionuclide) is complexed with a ligand useful for therapeutic purposes. A variety of useful ligands are known in the art. HEDP has a selective affinity for skeletal bone and thus is useful for diagnostic skeletal imaging or treatment of metastatic bone pain. Antibodies, both polyclonal and monoclonal, with selective affinities for tumor-associated antigens are useful for diagnosis or in situ radiotherapy of malignant tumors such as melanomas. Ligands with selective affinity for the hepatobiliary system, including 2,6-dimethylacetanilideiminodiacetic acid and the family of other imidoacetic acid group-containing analogs thereof (collectively referred to herein as "HIDA agents"), are useful for treatment of liver tumors. (See Wistow et al., J. Nuclear Medicine, 18:455–461 (1977), for a discussion of the HIDA family of ligands). Other ligands with specific affinities to sites in need of radiotherapy are known in the art and will continue to be discovered.

The radionuclide-to-ligand molar ratio will generally be between about $10^{-6}:1$ to about $10^{-1}:1$. The preferred ratio range is from $10^{-4}:1$ to about $10^{-2}:1$.

Ligands useful in the preparation of bone-scanning (imaging) agents are preferred for use in the preparation of therapeutic radiopharmaceuticals for treatment of pain due to bone metastases. The chemistry of such ligands causes them to localize almost exclusively on or within skeletal bone, and thus they provide the ability to target the radionuclide as desired. A broad range of mono-, di- and polyphosphonic acids and their pharmaceutically-acceptable salts are known to concentrate in the skeleton upon injection into a patient. Acceptable ligands include polyphosphates, pyrophosphates, phosphonates, diphosphonates and imidophosphonates. Preferred ligands are 1-hydroxyethylidene diphosphonate, methylene diphosphonate, (dimethylamino)methyl diphosphonate, methanehydroxydiphosphonate, and imidodiphosphonate.

The HIDA agents discussed above are one class of ligands which are particularly preferred for use according to the present invention. HIDA agents are known to complex with Tc-99m due to the presence of an iminodiacetic acid group. Preparation and stabilization of Re-186 or other derivatives of HIDA agents may be performed conveniently using the process of the present invention. The Re-186- or other-labeled HIDA derivatives then may be used to treat liver tumors.

The process of the present invention is particularly well suited for the preparation of stable, pre-labeled antibodies for use in the treatment of cancer and other diseases. For example, antibodies expressing affinity for specific tumors or tumor-associated antigens are labeled with a therapeutic radionuclide, either directly or via a bi-functional chelate, and the labeled antibodies are stabilized through lyophilization. Where a bi-functional chelate is used, it generally is covalently attached to the antibody. The antibodies used can be polyclonal or monoclonal, and the radionuclide-labeled antibodies can be prepared according to methods known in the art. The method of preparation will depend upon the type of radionuclide and antibody used. The stable, lyophilized, radiolabeled antibody merely is reconstituted with suitable diluent at the time of intended use, thus greatly simplifying the on site preparation process. The process of this invention can be applied to stabilize many types of pre-labeled antibodies, including, but not limited to, polyclonal and monoclonal antibodies to tumors associated with melanoma, colon cancer, breast cancer, prostate cancer, etc. Such antibodies are known in the art and are readily available.

The radiopharmaceutical complex which results from the method of this invention may be further purified after reconstitution, if desired. One method of purification is described in EP 250966, noted above. Other methods are known to those skilled in the art.

The radiopharmaceutical complex composition can include other components, if desired. Useful additional components include chemical stabilizers, lyophilization aids and microbial preservatives. Examples of chemical stabilizers include ascorbic acid, gentisic acid, reductic acid, and para-amino benzoic acid, among others. In some cases, these agents are beneficial in protecting the oxidation state of the radionuclide by preferential reaction with oxygen or by direct effect. Examples of lyophilization aids include those substances known to facilitate good lyophilization of the product. These aids are used to provide bulk and stability to the dried pellet and include lactose, dextrose, albumin, gelatin and sodium chloride, among others. Antimicrobial preservatives inhibit the growth of or kill microbial contaminants which are accidentally added to the product during preparation. Examples include methylparaben, propylparaben and sodium benzoate. These components generally are added to the composition after the complex has been formed between the ligand and the radionuclide but prior to lyophilization.

Once the radiopharmaceutical complex has been purified to the extent necessary for its final use, and any other desired components have been added, aliquots of the radiopharmaceutical complex are aseptically dispensed into sterile vials. The radioactive product then is lyophilized.

The lyophilization is carried out by pre-freezing the product, and then subjecting the frozen product to a high vacuum to effect essentially complete removal of water through the process of sublimation. The resultant pellet contains the complex in an anhydrous form which generally can be stored indefinitely, with practical consideration being given to the half-life of the radionuclide. The intended period of storage for radiopharmaceutical products is thus practically limited by the half-life of the radionuclides. In the case of Re-186, for example, the desired period of storage would range from 7 to about 30 days. Thus, this pellet can be shipped to the end users of the product and reconstituted with a diluent at the time of administration to the patient with very little effort on the part of the health care professional and/or nuclear pharmacist.

The following examples further illustrate the process of this invention, but are not meant to limit the scope of the invention in any way.

EXAMPLES

Example I

A. Preparation of Crude Re-186 HEDP Complex

1. The following ingredients were pre-weighed into a 10 mL serum vial. Alternately, a solution of these ingredients may be prepared and lyophilized.

| | |
|---|---|
| Etidronate sodium (HEDP) | 75 mg |
| $SnCl_2.2H_2O$ | 25 mg |
| Gentisic acid | 8.7 mg |

2. 1 mL of sodium perrhenate Re-186 injection was prepared to contain approximately 1 mg of rhenium.

3. Sufficient water was added to dilute the Re-186 perrhenate solution to 3 mL.

4. The Re-186 perrhenate solution was added to the vial in step 1 which contains etidronate sodium, stannous chloride and gentisic acid.

5. The vial contents were mixed thoroughly for 1 minute and the pH was adjusted to 3.4 to 3.6 using NaOH and/or HCl.

6. The complex solution was sparged for 3 minutes with $N_2$ or Ar gas.

7. A 20 mm 890 gray/Teflon faced stopper was applied to the vial and sealed with a 20 mm tear-off crimp cap.

8. The vial and contents were heated to 100° C for 10 minutes. This completed the preparation of the crude Re-186 HEDP complex.

B. Purification of Re-186 HEDP Complex 1. 3 mM Gentisic Acid was prepared:

| | |
|---|---|
| Gentisic Acid | 46.2 mg |
| $NaH_2PO_4.H_2O$ | 28.0 mg |
| NaOH/HCl | pH 5.3 to 5.5 |
| Water for injection | 100.0 mL |

2. A QMA Sep-Pak cartridge was rinsed with 10 mL of 3 mM gentisic acid.

3. The crude Re-186 HEDP complex was diluted to 20 mL with 3 mM gentisic acid.

4. The crude Re-186 HEDP complex was passed through the QMA Sep-Pak Cartridge at a flow rate of about 1 drop per second.

5. The reaction vial was rinsed with 10 mL of 3 mM gentisic acid; the rinse was passed through the QMA Sep-Pak cartridge.

6. The column was fractionally eluted with a solution prepared to contain 3 mM gentisic acid, 0.01M disodium etidronate, and 0.3M NaCl.

7. The first 1.0 mL coming off of the column was discarded and the next 3 mL of eluate was collected. The 3 mL collected fraction was sparged with Ar or other inert gas.

C. Lyophilization of Purified Re-186 HEDP Complex

1. The 3 mL solution of Re-186 HEDP complex was diluted with a freshly prepared diluent which was made up to contain:

| | |
|---|---|
| $SnCl_2.2H_2O$ | 203 mg (Max.) |
| NaCl | 1.75 g |
| Disodium etidronate | 250.0 mg |
| Gentisic Acid | 46.2 mg |
| NaOH/HCl | pH 5.3 to 5.4 |
| Water for Injection | 100.0 mL |

The solution was diluted to a final concentration of 50 mCi/mL with diluent.

2. 1 mL of the purified, diluted complex was dispensed into 10 mL, washed, siliconized and sterilized glass tubing vials.

3. West S87J-890 Gray lyophilization stoppers were partially inserted into the vials, and placed on precooled shelf of lyophilizer.

4. The complex was frozen to a temperature of −30° C. or colder, the condenser was cooled to −50° C. or colder and a vacuum was applied.

5. Application of shelf heat was begun when chamber pressure had declined to 90 microns or less.

6. Shelf heat was increased at a rate of 6° C./hour until a final product temperature of 30° C. was reached. The temperature was held for 2 hours. Note: Each lyophilizer has different heat transfer rates and condenser temperature characteristics; the rate of shelf heat increase may require adjustment for each lyophilizer in order to avoid product collapse (melt back during lyophilization).

7. At completion of the cycle, Ar gas was bled in for 5 minutes before shutting off the vacuum pump. Inlet of Ar gas was continued until the chamber pressure reached ambient or slightly below ambient pressure.

8. The stoppering mechanism was activated to insert stoppers to their fully closed position.

9. Stoppered vials were removed from lyophilizer and aluminum crimp seals were applied.

D. Quality Evaluation of Re-186 HEDP Complex

Vials of the Re-HEDP complex were reconstituted and tested for radiochemical purity and biodistribution at 2 days and 8 days following manufacture of material. Reconstitution of the samples was carried out by simple addition of 2–3 mL of water for injection. The ingredients dissolved immediately to yield a clear colorless solution. Two different chromatography tests were run to determine radiochemical purity. The first chromatography system employed Whatman 3MM paper which was developed by the ascending movement of acetone. In this system free perrhenate ($ReO_4^-$) migrates to an Rf of about 0.9 while Re-186 HEDP complexes and insoluble ReO, remain at the origin. The second chromatography method uses Whatman 3 MM developed with 0.9% sodium chloride/0.1M etidronate sodium solution. In this system, both the Re-186 HEDP complex and free perrhenate migrate near the solvent front while ReO$_2$ remains at the origin. By the combined use of these two systems it becomes possible to measure the level of Re-186 activity present as Re-186 HEDP complex, free perrhenate and rhenium dioxide.

In addition, a portion of each sample was injected into test rats in order to determine its biological distribution. Groups of 3 rats were injected with each sample. A constant injection volume of 0.3 mL was used. All test rats were female weighing about 200 g. Three hours after injection the rats were sacrificed and the following samples were obtained: femur, blood, kidney, and muscle. The samples were weighed and the level of Re-186 radioactivity present in each sample was measured. Results were expressed as a percent of injected dose found per gram of tissue. The findings are summarized in the following table:

| Samp. Age(d) | % ReO$_2$ | % ReO$_4$ | % g Bone | %/g Blood | %/g Kidney | Ratio Bone/ Bld. | Ratio Bone/ Mus. |
|---|---|---|---|---|---|---|---|
| 2 | 0.1 | 1.6 | 1.51 | 0.1 | 1.19 | 15.21 | 235.1 |
| 8 | 0.0 | 1.4 | 1.8 | .081 | 0.89 | 22.36 | 195.1 |

The results show that the lyophilized Re-186 HEDP complex remained unchanged, with respect to radiochemical purity and animal bio-distribution throughout a storage interval of 8 days from manufacture.

EXAMPLE 2

A. Preparation of Crude Re-186 HEDP Complex

Preparation of the crude Re-186 HEDP complex was carried out in the same manner described in Example 1.

B. Purification of Re-186 HEDP Complex

Purification of Re-186 Complex was performed identically to the procedures outlined in Example 1.

C. Lyophilization of Purified Re-186 HEDP Complex 1. 0.25 mL (50 mCi) of the purified, undiluted complex was dispensed into 10 mL, washed, siliconized and sterilized glass tubing vials.
2. The vials were stoppered and lyophilized containing liquid Re-186 HEDP complex in accordance with the methods described in Example 1.

D. Quality Evaluation of Re-186 HEDP Complex

The lyophilized vials were reconstituted and evaluated using identical radiochemical purity test procedures as described in Example 1, except for the fact that the test for ReO$_2$ was not performed. In addition, similar bio-distribution tests were performed on these samples. The diluent used to reconstitute the lyophilized vials of Re-186 HEDP complex was freshly prepared to contain the following additives:

| | |
|---|---|
| SnCl$_2$.2H$_2$O | 203 mg (Max.) |
| NaCl | 1.75 g |
| Etidronate sodium | 250 mg |
| Gentisic acid | 46.2 mg |
| NaOH/HCl | pH 5.3 to 5.4 |
| Water for injection | 100.0 mL |

| Samp. Age(d) | % ReO$_2$ | % ReO$_4$ | % g Bone | %/g Blood | %/g Kidney | Ratio Bone/ Bld. | Ratio Bone/ Mus. |
|---|---|---|---|---|---|---|---|
| 2 | n.d | 0.0 | 2.23 | 0.1 | 1.16 | 23.47 | 327.4 |
| 8 | n.d | 0.5 | 2.08 | 0.11 | 1.28 | 19.98 | 172.9 |

The results show that the lyophilized Re-186 HEDP complex remained unchanged, with respect to radiochemical purity and animal bio-distribution, throughout a storage interval of 6 days from manufacture.

EXAMPLE 3

Preparation of Re-186 Labelled Antibodies

A. Preparation of the Re-186 MAGG* Ligand Complex

1. Prepare 0.5 mL of sodium perrhenate Re-186 solution containing between 100–500 mCi of Re-86.
2. Dissolve the bi-functional chelate (MAGG ligand) in isopropyl alcohol and add to the sodium perrhenate Re-186 solution.
3. Heat to 85° C. for 30 minutes.
4. Cool and perform an in-process chromatography test to determine yield and purity of the Re-186 - MAGG ligand ester.

*S-ethoxyethyl mercaptoacetyl glycylglycyl-γ-aminobutyric acid-2,3,5,6-tetrafluorophenylester, formula:

B. Conjugation of Re-186 MAGG to the Antibody

5. Add carbonate solution to the Re-186 MAGG ester and then add 25 to 75 mg of the monoclonal antibody.
6. Add additional carbonate and incubate for 12 minutes (during which time the ester portion of the Re-186 MAGG complex reacts with the antibody).
7. Perform quality control chromatography, and add lysine solution.

C. Purification of the Labeled Antibody

8. Purify the labeled antibody preparation by passing through an acrylamide chromatography column. Collect in a solution of human serum albumin.

D. Dispense and Lyophilize

9. Assay and dilute to desired concentration (mCi Re-186/mL).
10. Dispense aliquots into serum vials, freeze and lyophilize.
11. Prepare a vial for administration by reconstitution of the lyophilized preparation using 0.9% sodium chloride injection.

I claim:

1. A method of preparing a stable radioactive therapeutic radiopharmaceutical composition which comprises providing a therapeutic amount of an alpha- or beta-emitting radionucliden forming a complex between said therapeutic amount of said radionuclide and a ligand in an aqueous medium, and then lyophilizing the medium so as to form a stable radioactive therapeutic radiopharmaceutical composition.

2. The method of claim 1 wherein the radionuclide comprises rhenium-186, rhenium-188, iodine-131, samarium-153 or strontium-89.

3. The method of claim 1 wherein the ligand has a selective affinity for skeletal bone.

4. The method of claim 3 wherein the ligand comprises a polyphosphate, pyrophosphate, phosphonate, diphosphonate or imidodiphosphate.

5. The method of claim 3 wherein the ligand comprises a diphosphonate.

6. The method of claim 5 wherein the ligand comprises hydroxyethylidene diphosphonate.

7. The method of claim 6 wherein the radionuclide comprises rhenium-186.

8. The method of claim 1 wherein the ligand has a selective affinity for tumor cells.

9. The method of claim 1 wherein the ligand has a selective affinity for a tumor-associated antigen.

10. The method of claim 1 wherein the ligand comprises a monoclonal antibody.

11. The method of claim 8 wherein the ligand comprises a monoclonal antibody.

12. The method of claim 1 wherein the ligand comprises a polyclonal antibody.

13. The method of claim 8 wherein the ligand comprises a polyclonal antibody.

14. The method of claim 8 wherein the ligand comprises an antibody fragment.

15. The method of claim 11 wherein the radionuclide comprises rhenium-186.

16. The method of claim 13 wherein the radionuclide comprises rhenium-186.

17. The method of claim 10 wherein the radionuclide is bound to the antibody or antibody fragment via a bifunctional chelate.

18. The method of claim 12 wherein the radionuclide is bound to the antibody or antibody fragment via a bifunctional chelate.

19. The method of claim 15 wherein the ligand comprises MAGG.

20. The method of claim 16 wherein the ligand comprises MAGG.

21. The method of claim 1 wherein the ligand has a selective affinity for the hepatobiliary system.

22. The method of claim 21 wherein the ligand is 2,6-dimethylacetanilide iminodiacetic acid or a derivative thereof.

23. The method of claim 1 wherein the solution comprises a lyophilization aid.

24. The method of claim 23 wherein the lyophilization aid comprises lactose, dextrose, albumin, gelatin or sodium chloride.

25. The method of claim 1 wherein the radionuclide has a half-life of at least about 12 hours.

26. A radiopharmaceutical composition prepared by the method of claim 1.

27. A radiopharmaceutical composition prepared by the method of claim 10.

28. A radiopharmaceutical composition prepared by the method of claim 12.

29. A stable radioactive radiopharmaceutical composition comprising a lyophilized complex of rhenium-186 and a bio-compatible ligand wherein rhenium-186 is present in a therapeutic amount.

30. A stable radioactive radiopharmaceutical composition comprising a lyophilized complex of rhenium-188 and a bio-compatible ligand wherein rhenium-188 is present in a therapeutic amount.

31. A composition according to claim 29 wherein the ligand comprises a protein.

32. A composition according to claim 30 wherein the ligand comprises a protein.

33. A composition according to claim 31 wherein the protein comprises an antibody.

34. A composition according to claim 32 wherein the protein comprises an antibody.

35. A method of preparing a stable radioactive therapeutic radiopharmaceutical composition which comprises providing a therapeutic amount of rhenium-186, forming a complex between said therapeutic amount of rhenium-186 and a ligand in an aqueous medium, and then lyophilizing the medium so as to form a stable radioactive therapeutic radiopharmaceutical composition.

36. A method of preparing a stable radioactive therapeutic radiopharmaceutical composition which comprises providing a therapeutic amount of rhenium-188, forming a complex between said therapeutic amount of rhenium-188 and a ligand in an aqueous medium, and then lyophilizing the medium so as to form a stable radioactive therapeutic radiopharmaceutical composition.

37. A method of preparing a stable radioactive therapeutic radiopharmaceutical composition which comprises providing a therapeutic amount of samarium-153, forming a complex between said therapeutic amount of samarium-153 and a ligand in an aqueous medium, and then lyophilizing the medium so as to form a stable radioactive therapeutic radiopharmaceutical composition.

38. A method of preparing a stable radioactive therapeutic radiopharmaceutical composition which comprises providing a therapeutic amount of strontium-89, forming a complex between said therapeutic amount of strontium-89 and a ligand in an aqueous medium, and then lyophilizing the medium so as to form a stable radioactive therapeutic radiopharmaceutical composition.

* * * * *